United States Patent
Kim et al.

(10) Patent No.: US 10,801,009 B2
(45) Date of Patent: Oct. 13, 2020

(54) COSMETIC COMPOSITION FOR IMPROVING CONDITION OF SKIN, CONTAINING CELL CULTURE MEDIUM, EPIDERMAL GROWTH FACTOR AND BOVINE SERUM ALBUMIN

(71) Applicant: BIOCOZ GLOBAL KOREA CORP., Seoul (KR)

(72) Inventors: Chan Wha Kim, Seoul (KR); Young Joon Kim, Tenafly, NJ (US); Hyun Jung Kim, Seoul (KR)

(73) Assignee: BIOCOZ GLOBAL KOREA CORP., Seoul (KR)

(*) Notice: Subject to any disclaimer, the term of this patent is extended or adjusted under 35 U.S.C. 154(b) by 0 days.

(21) Appl. No.: 15/527,046

(22) PCT Filed: Nov. 17, 2015

(86) PCT No.: PCT/KR2015/012344
§ 371 (c)(1),
(2) Date: May 16, 2017

(87) PCT Pub. No.: WO2016/080732
PCT Pub. Date: May 26, 2016

(65) Prior Publication Data
US 2017/0355952 A1    Dec. 14, 2017

Related U.S. Application Data

(60) Provisional application No. 62/080,708, filed on Nov. 17, 2014.

(51) Int. Cl.
*C12N 5/00* (2006.01)
*A61Q 19/08* (2006.01)
*A61K 8/64* (2006.01)
*A61K 38/38* (2006.01)
*A61Q 19/00* (2006.01)
*A61K 38/18* (2006.01)
*C12N 5/07* (2010.01)
*C12Q 1/68* (2018.01)

(52) U.S. Cl.
CPC .............. *C12N 5/0018* (2013.01); *A61K 8/64* (2013.01); *A61K 38/1808* (2013.01); *A61K 38/385* (2013.01); *A61Q 19/00* (2013.01); *A61Q 19/08* (2013.01); *C12N 5/0037* (2013.01); *C12N 5/06* (2013.01); *C12Q 1/68* (2013.01); *C12N 2500/14* (2013.01); *C12N 2500/16* (2013.01); *C12N 2500/46* (2013.01); *C12N 2500/76* (2013.01); *C12N 2501/11* (2013.01)

(58) Field of Classification Search
CPC ...... C12N 5/0018; C12N 5/0037; C12N 5/06; C12N 2500/14; C12N 2500/16; C12N 2500/46; C12N 2500/76; C12N 2501/11; A61K 8/64; A61K 38/1808; A61Q 19/00; A61Q 19/08; C12Q 1/68
USPC ............................................. 435/405
See application file for complete search history.

(56) References Cited

U.S. PATENT DOCUMENTS

| 5,712,163 A | 1/1998 | Parenteau et al. |
| 6,039,760 A | 3/2000 | Eisenberg |
| 2005/0226853 A1 | 10/2005 | Conrad et al. |
| 2008/0261259 A1 | 10/2008 | Morris |
| 2009/0202654 A1* | 8/2009 | Nixon .................... A61K 8/985 424/574 |

FOREIGN PATENT DOCUMENTS

KR    10-2014-0103759 A    8/2014

OTHER PUBLICATIONS

Pierce, Protein stability and storage, Sep. 2005, Available Online at: www.indiana.edu/~lchenlab/protocol_files/protein_storage.pdf.*
HiMedia, Product Information, Dulbecco's Modified Eagle Medium/Nutrient Mixture F-12 Ham (DMEM/F12, 3:1 Mixture), Jan. 2013, Available Online at: himedialabs.com/TD/AT189.pdf.*
International Searching Authority, International Search Report of PCT/KR2015/012344 dated Feb. 29, 2016 [PCT/ISA/210].

* cited by examiner

*Primary Examiner* — Jennifer M. H. Tichy
(74) *Attorney, Agent, or Firm* — Sughrue Mion, PLLC

(57) ABSTRACT

The present invention relates to: a cosmetic composition for improving the condition of the skin, containing, as active ingredients, a cell culture medium, an epidermal growth factor and a bovine serum albumin; a method for improving the condition of the skin by using the same; and a method for preventing or treating skin diseases. According to the present invention, the cosmetic composition can exhibit excellent wrinkle-reducing and wound-healing effects even when only a small amount of EGF is used, and thus can be useful in improving the condition of the skin or in preventing or treating skin diseases.

10 Claims, 12 Drawing Sheets

[Fig. 1]
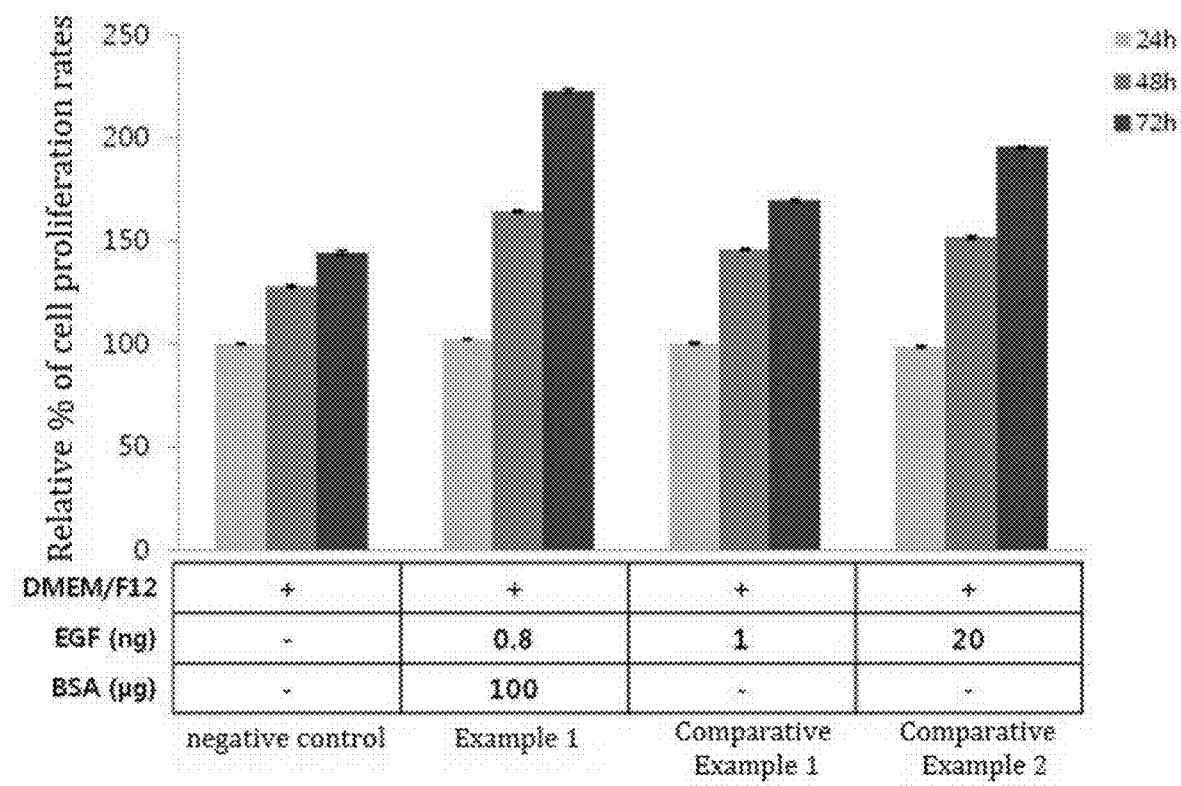

[Fig. 2]
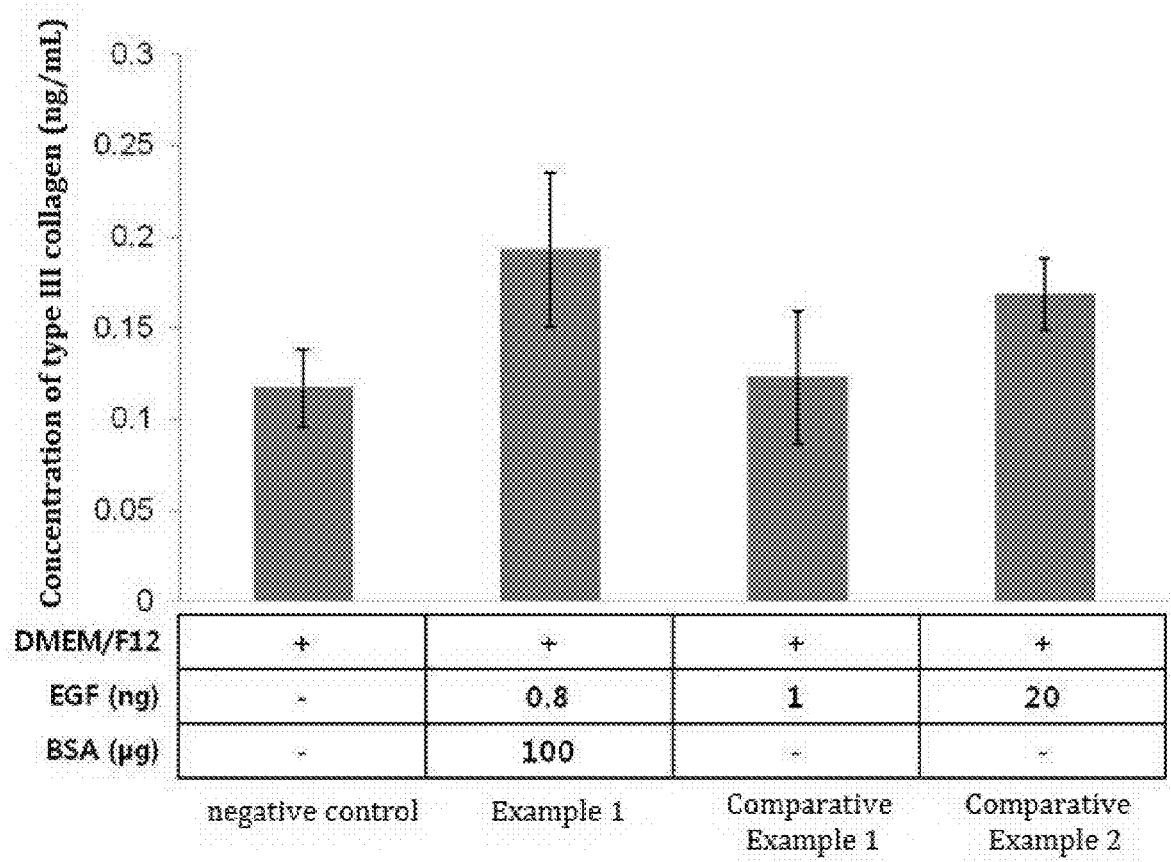

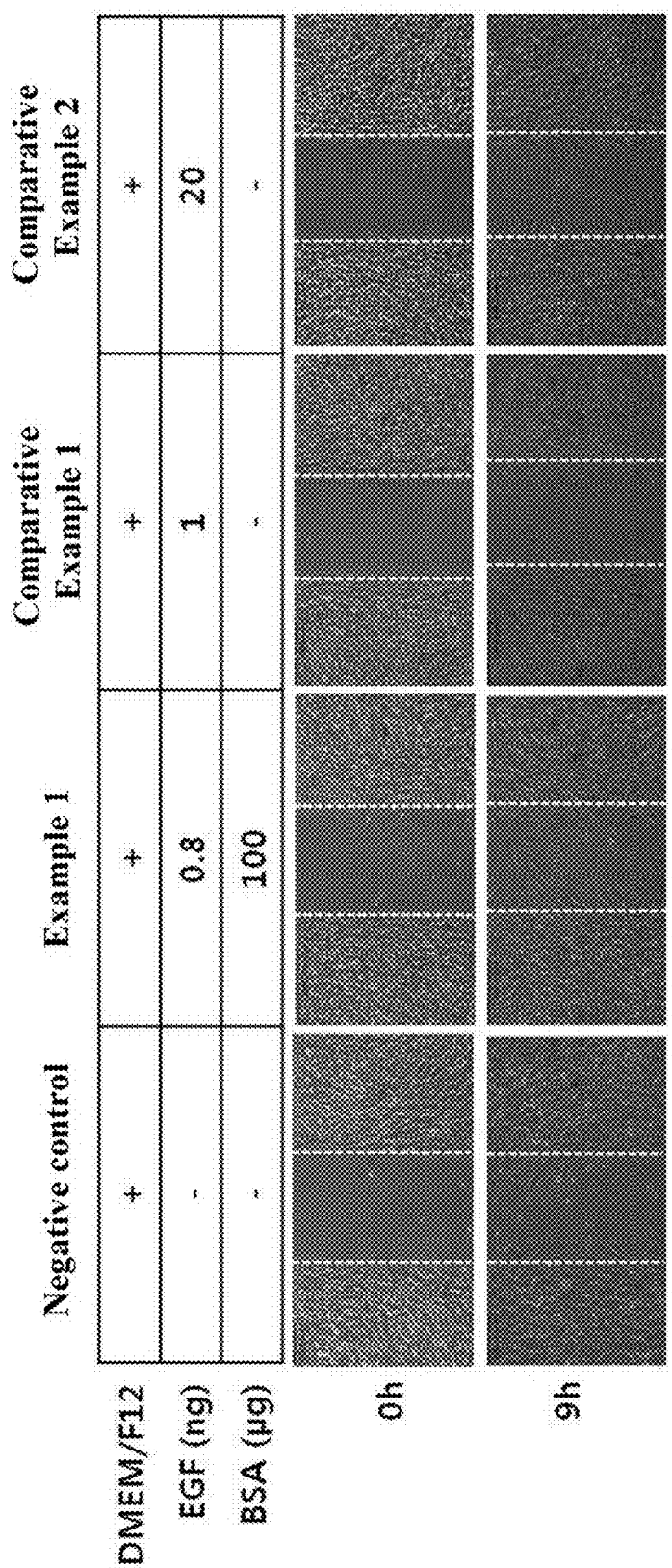
[Fig. 3]

[Fig. 4]
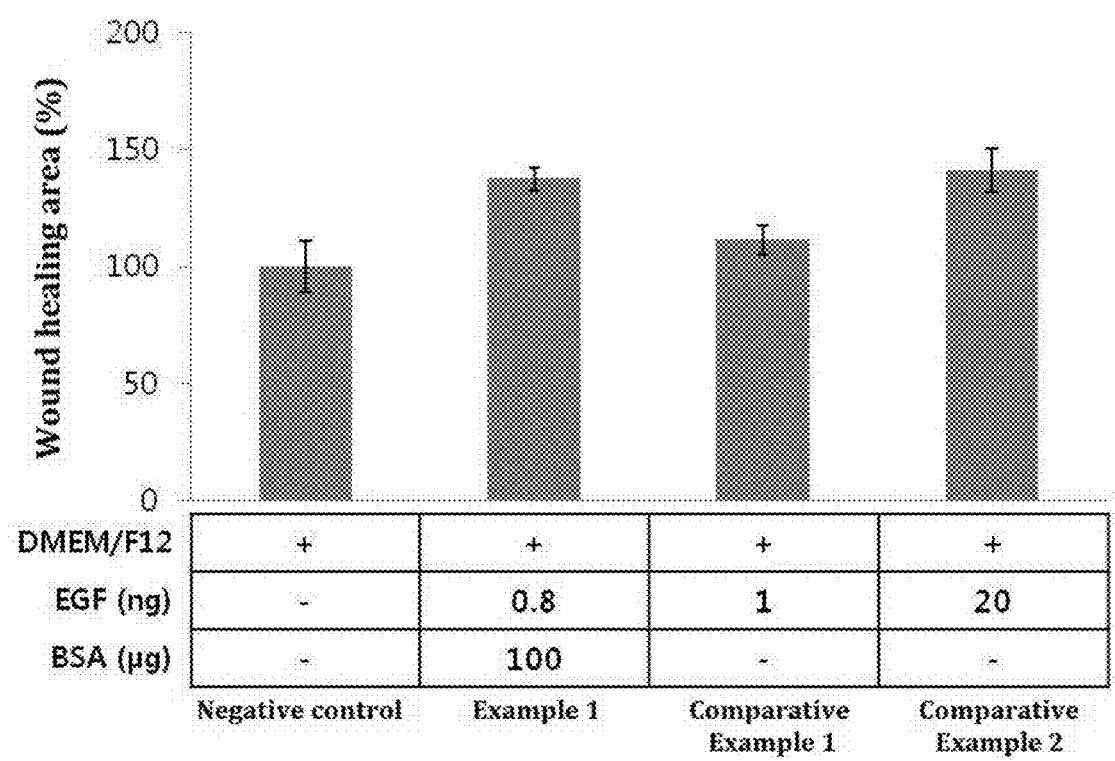

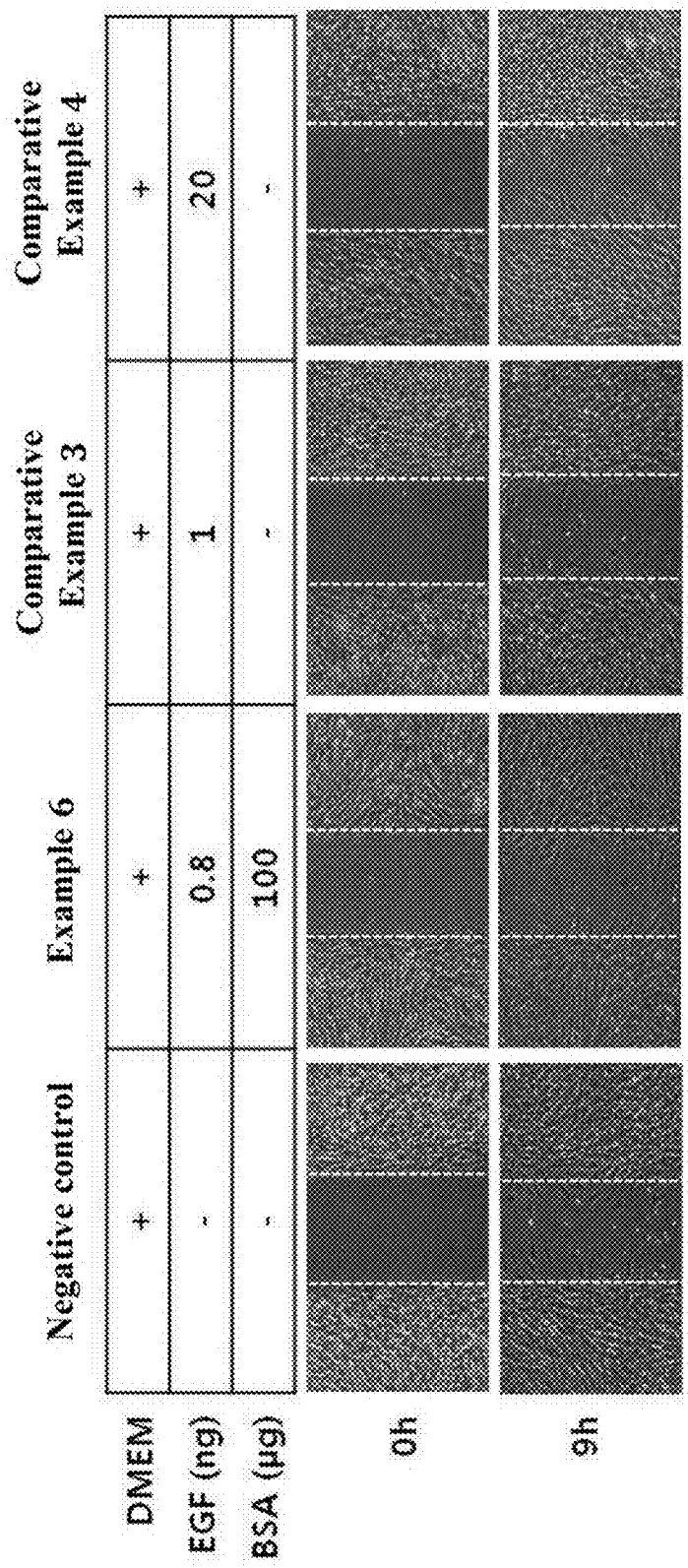
[Fig. 5]

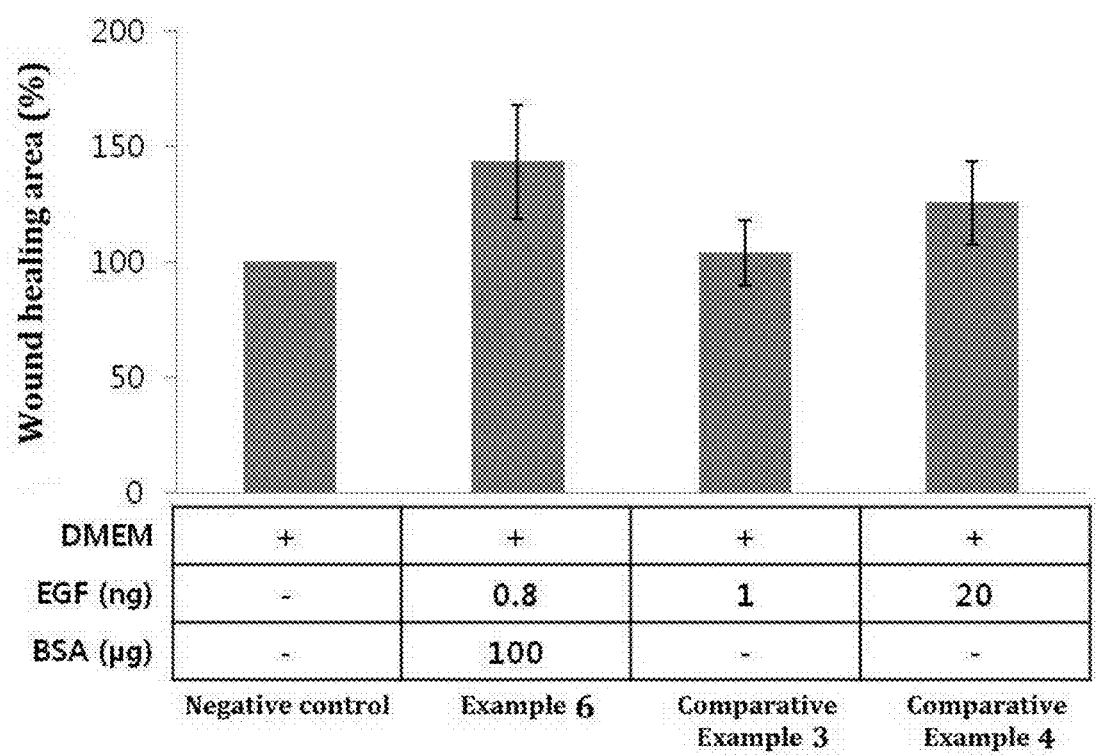
[Fig. 6]

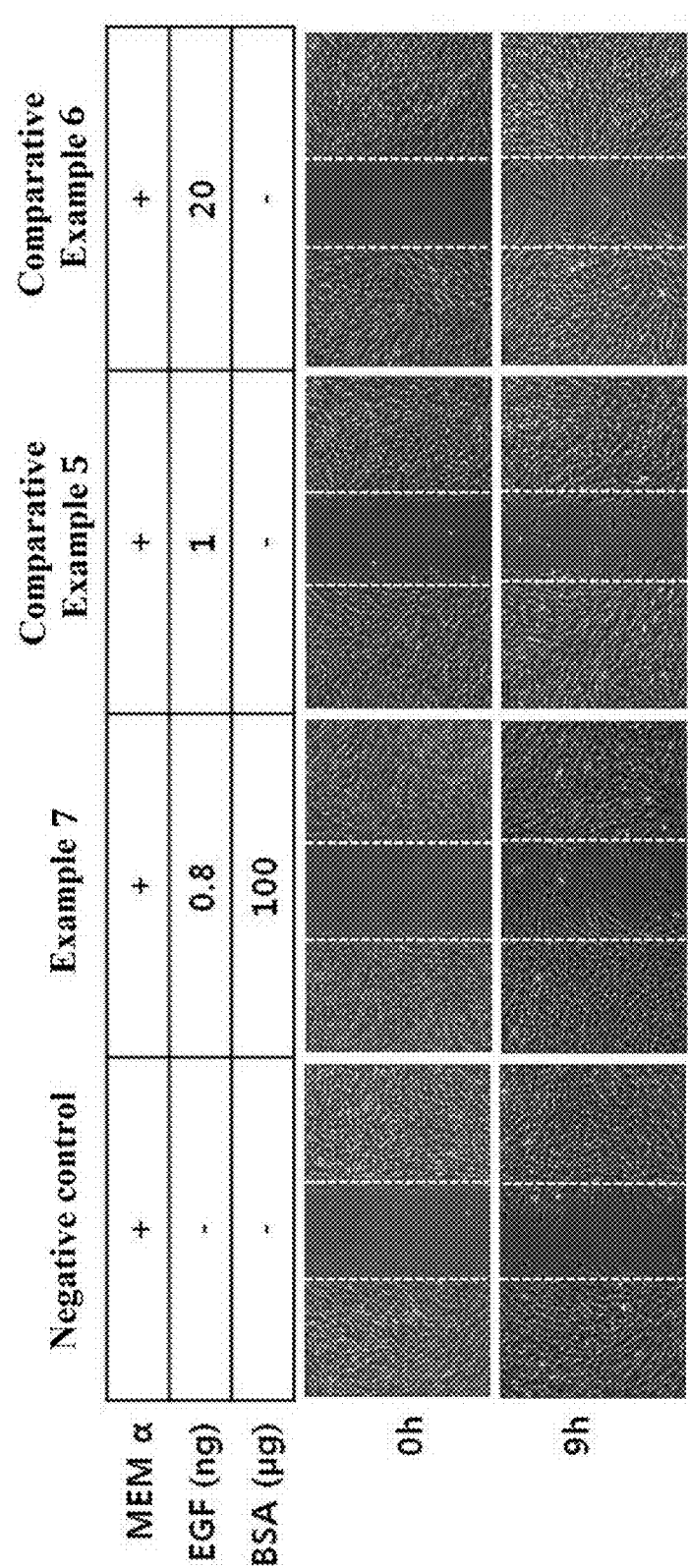

[Fig. 8]
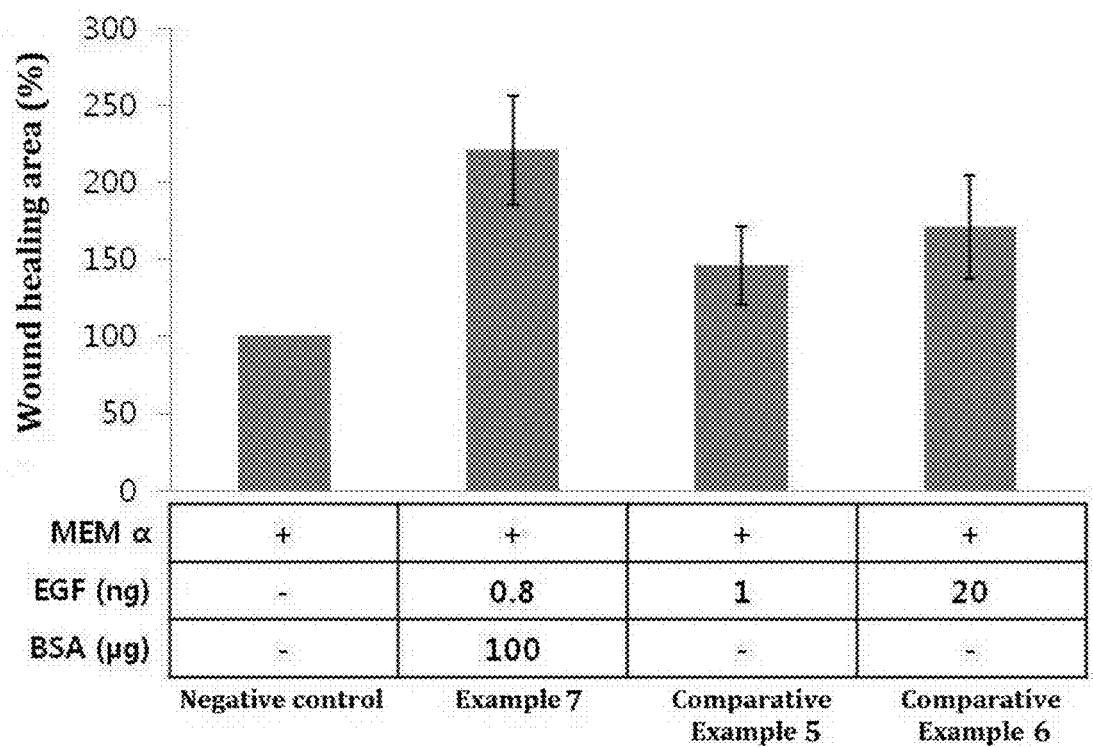

[Fig. 9]
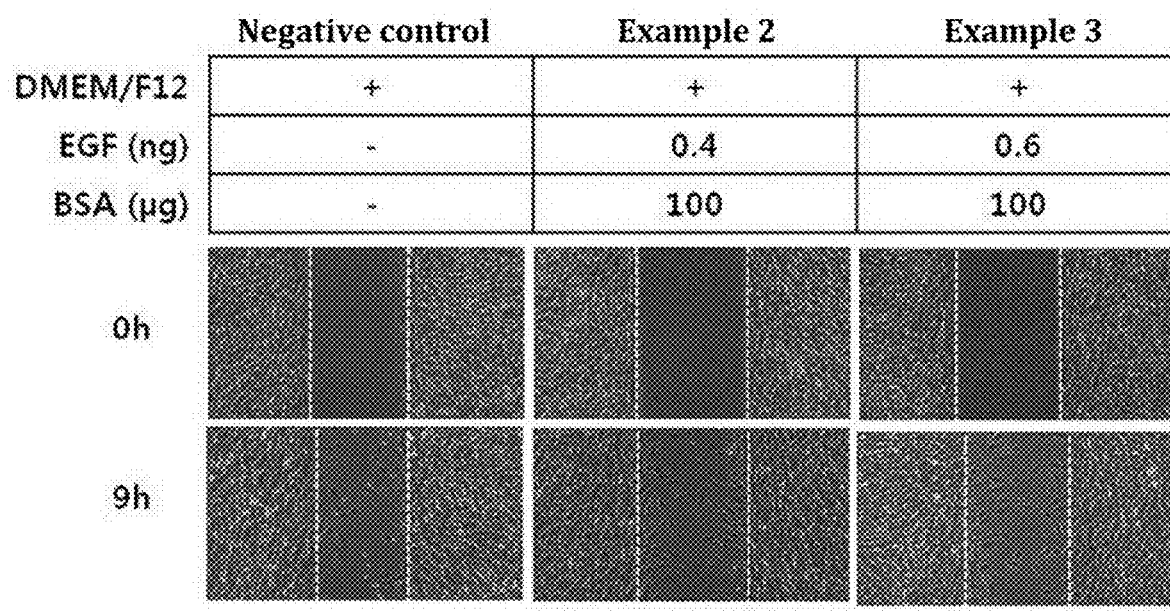
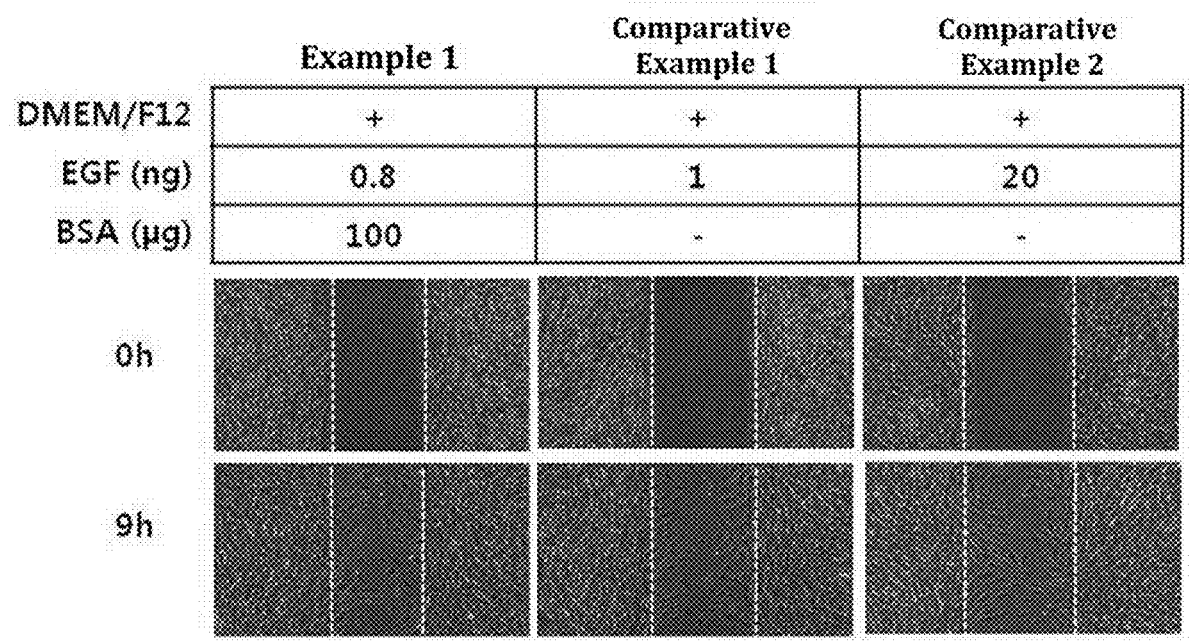

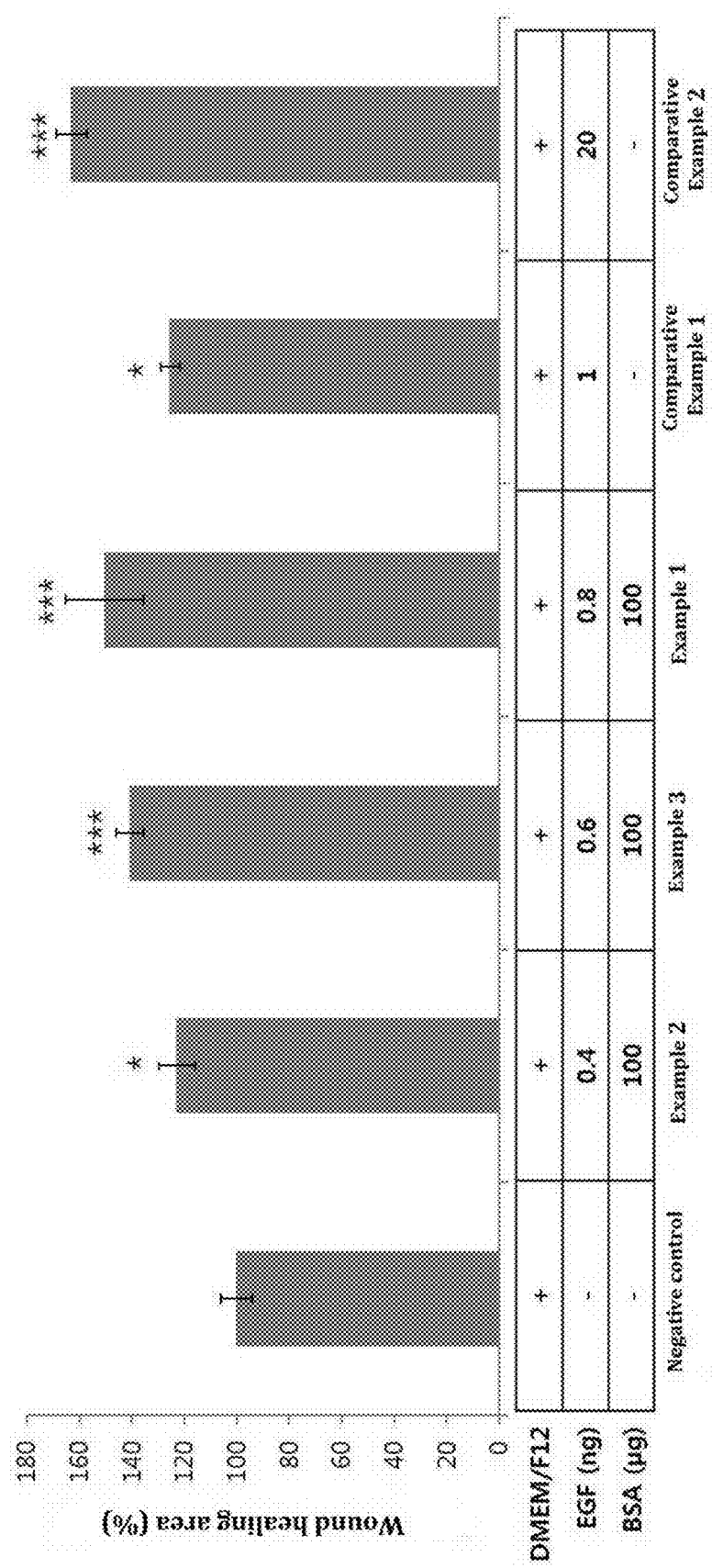
[Fig. 10]

[Fig. 11]

| | Negative control | Example 4 | Example 1 |
|---|---|---|---|
| DMEM/F12 | + | + | + |
| EGF (ng) | - | 0.8 | 0.8 |
| BSA (µg) | - | 10 | 100 |
| 0h | | | |
| 9h | | | |

| | Example 5 | Comparative Example 1 | Comparative Example 2 |
|---|---|---|---|
| DMEM/F12 | + | + | + |
| EGF (ng) | 0.8 | 1 | 20 |
| BSA (µg) | 1000 | - | - |
| 0h | | | |
| 9h | | | |

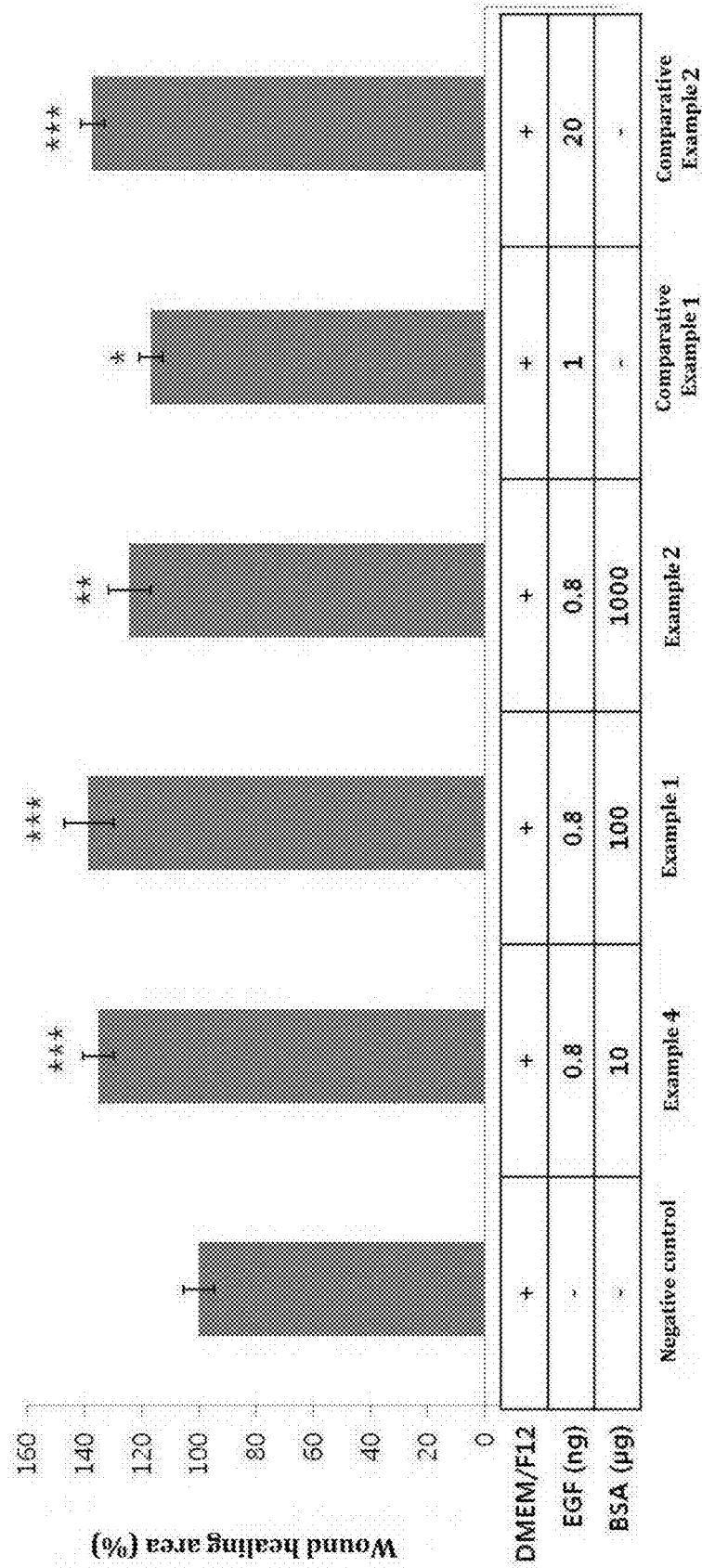

COSMETIC COMPOSITION FOR IMPROVING CONDITION OF SKIN, CONTAINING CELL CULTURE MEDIUM, EPIDERMAL GROWTH FACTOR AND BOVINE SERUM ALBUMIN

TECHNICAL FIELD

The present invention relates to a cosmetic composition for improving the condition of the skin, containing a cell culture medium, an epidermal growth factor and a bovine serum albumin; a method for improving the condition of the skin by using the same; and a method for preventing or treating skin diseases.

BACKGROUND ART

Epidermal growth factor (EGF) is a typical component that promotes collagen synthesis, thereby showing the effect of wrinkle improvement. However, since excessive use of EGF causes a problem of stimulating the growth and migration of cancer cells, the usage amount of EGF is restricted for safety reasons. Therefore, it is needed to develop a composition capable of maximizing its effect even with a small amount of EGF.

Meanwhile, the cells constituting skin cells are a kind of animal cells such as keratinocytes and fibroblasts. Typical composition of a medium for culturing the above cells includes DMEM (Dulbecco's Modified Eagle's medium) and fetal bovine serum (FBS).

Serum is known to play a role in growth promotion, nutrient supply, and protection of cells from oxidation and toxins. When the serum is excluded in cell culture, the cell culture itself is hardly achieved, and thus the serum is recognized as an essential component for growth and proliferation of cells. In addition, it is known that the serum albumin contained in the serum accounts for about 55-60% of the total serum protein, and the albumin attracts water to maintain the water content in the blood, thereby enhancing skin elasticity. Currently, the most widely used serum components are FBS and FCS (fetal calf serum).

However, it has recently been reported that FBS may cause human mad cow disease. This may threaten the safety of the tester and also there is a problem in terms of animal protection since serum is taken directly from the bovine fetus. In addition, since FBS is expensive, there is a disadvantage of raising the cost of a medium.

Accordingly, it is continuously needed to develop a composition that is safe to a living body and exhibits excellent effects of improving skin conditions, e.g., wrinkle improvement, skin regeneration, and wound healing, without containing FBS.

DISCLOSURE OF INVENTION

Technical Problem

Accordingly, an object of the present invention is to provide a cosmetic composition that is safe to a living body and exhibits excellent effects of improving skin conditions, e.g., wrinkle improvement, skin regeneration, and wound healing, and a method for improving a skin condition using the cosmetic composition.

Another object of the present invention is to provide a pharmaceutical composition having the same composition as the above cosmetic composition, and a method for preventing or treating a skin disorder using the same.

Solution to Problem

In accordance with the object of the present invention, there is provided a cosmetic composition for improving a skin condition comprising as the effective components:
a) a cell culture medium;
b) 0.4 to 0.8 ng/mL of epidermal growth factor (EGF); and
c) 10 to 1,000 μg/mL of bovine serum albumin (BSA).

In accordance with another object of the present invention, there is provided a method for improving a skin condition using the above cosmetic composition.

In accordance with still another object of the present invention, there is provided a use of the cosmetic composition in preparing cosmetics for improving a skin condition.

In accordance with another object of the present invention, there is provided a pharmaceutical composition for preventing or treating a skin disorder comprising:
a) a cell culture medium;
b) 0.4 to 0.8 ng/mL of epidermal growth factor (EGF); and
c) 10 to 1,000 μg/mL of bovine serum albumin (BSA).

In accordance with still another object of the present invention, there is provided a method for preventing or treating a skin disorder using the pharmaceutical composition.

In accordance with still another object of the present invention, there is provided a use of the pharmaceutical composition in preparing a drug for preventing or treating a skin disorder.

Advantageous Effects of Invention

A composition of the present invention is not only effective for skin condition improvement such as wrinkle improvement, skin regeneration, wound healing, etc., but also useful in preventing or treating a skin disorder such as atopic dermatitis, allergy, and the like.

BRIEF DESCRIPTION OF DRAWINGS

The above and other objects and features of the present invention will become apparent from the following descriptions of the invention, when taken in conjunction with the accompanying drawings.

FIG. 1 is a graph showing the cell proliferation rates depending on time after treatment of human fibroblasts with the compositions of Example 1 and Comparative Examples 1 and 2.

FIG. 2 is a graph showing the type III collagen synthesis capability after treatment of human fibroblasts with the compositions of Example 1 and Comparative Examples 1 and 2.

FIGS. 3 and 4 provide cell images before and after treatment of human fibroblasts with the compositions of Example 1 and Comparative Examples 1 and 2, and a graph showing wound healing capacity quantified as cell migration rates, respectively.

FIGS. 5 and 6 provide cell images before and after treatment of human fibroblasts with the compositions of Example 6 and Comparative Examples 3 and 4, and a graph showing wound healing capacity quantified as cell migration rates, respectively.

FIGS. 7 and 8 provide cell images before and after treatment of human fibroblasts with the compositions of Example 7 and Comparative Examples 5 and 6, and a graph showing wound healing capacity quantified as cell migration rates, respectively.

FIGS. 9 and 10 provide cell images before and after treatment of human fibroblasts with the compositions of Examples 1 to 3 and Comparative Examples 1 and 2, and a graph showing wound healing capacity quantified as cell migration rates, respectively.

FIGS. 11 and 12 provide cell images before and after treatment of human fibroblasts with the compositions of Examples 1, 4 and 5 and Comparative Examples 1 and 2, and a graph showing wound healing capacity quantified as cell migration rates, respectively.

BEST MODE FOR CARRYING OUT THE INVENTION

Hereinafter, the present invention will be described in more detail.

The present invention provides a cosmetic composition for improving a skin condition comprising: a) a cell culture medium; b) 0.4 to 0.8 ng/mL of epidermal growth factor (EGF); and c) 10 to 1,000 μg/mL of bovine serum albumin (BSA).

The composition according to the present invention activates or promotes the increase of fibroblasts present in a skin when applied to a human skin, and promotes collagen synthesis to improve a skin condition by showing the effects of wrinkle improvement, inhibition of skin aging, skin elasticity improvement, healing of a wound such as scar, skin regeneration, etc.

A cosmetic composition of the present invention can be used for protecting a skin from functional deterioration or loss of a skin cell, or for improving a skin condition; or preventing or treating a skin disorder Such protection of a skin from functional deterioration or loss of a skin cell or improvement of a skin condition may comprise inhibition of wrinkle occurrence, inhibition of skin aging, improvement of skin elasticity, skin regeneration, injury or wound healing, corneal regeneration, and the like.

The skin disorder may comprise inflammatory skin disorders such as atopic dermatitis, allergy, skin eczema, acne, psoriasis, and the like.

Therefore, the present invention provides a method for improving a skin condition using such cosmetic composition.

In addition, the present invention provides a use of the cosmetic composition in preparing cosmetics for improving a skin condition.

The method may comprise a step of applying the cosmetic composition to a skin of a subject in need of improvement of a skin condition.

A cosmetic composition of the present invention comprises a cell culture medium.

The cell culture medium may be a medium capable of culturing mammalian cells such as fibroblasts, keratinocytes, melanocytes, stem cells, muscle cells, germ cells and immune cells.

In the present invention, a cell culture medium selected from the group consisting of DMEM/F-12, DMEM and MEM α may be used.

The cell culture medium may be an FBS-free medium. In the present invention, it is possible to promote excellent cell growth and proliferation without containing FBS as a nutrient component, which is expensive and may cause safety problems.

A cosmetic composition of the present invention comprises EGF as a cytokine.

The EGF may be comprised in an amount of 0.4 to 0.8 ng/mL, preferably 0.4 to 0.6 ng/mL, 0.6 to 0.8 ng/mL, 0.4 to 0.5 ng/mL, 0.5 to 0.8 ng/mL, 0.6 to 0.7 ng/mL or 0.5 to 0.7 ng/mL.

A composition of the present invention enables cell culture with a superior cell growth rate as compared to a conventional serum-containing medium by adding EGF to a cell culture medium.

In particular, a composition of the present invention does not have any adverse effect on cell growth even if EGF is contained in a small amount of 0.4 to 0.8 ng/mL. In addition, the composition of the present invention can promote collagen synthesis, and show a skin regeneration effect such as wound healing. This is a synergistic effect of the together cosmetic composition of the present invention which contains EGF and BSA.

A cosmetic composition of the present invention contains BSA as a nutritional component.

The BSA may be comprised in an amount of 10 to 1,000 μg/mL, preferably 10 to 100 μg/mL, 10 to 500 μg/mL, 100 to 500 μg/mL, 500 to 1,000 μg/mL, 50 to 200 μg/mL or 80 to 120 μg/mL.

A cosmetic composition of the present invention may further comprise a component selected from the group consisting of an amino acid, a vitamin, a carbon source, an inorganic salt, and a combination thereof.

The amino acid may be an amino acid component used in a conventional animal cell culture medium, and may be selected from the group consisting of, for example, glycine, L-alanine, L-arginine hydrochloride, L-asparagine-monohydrate, L-aspartic acid, L-cysteine hydrochloride-monohydrate, L-cysteine 2HCl, L-glutamic acid, L-glutamine, L-histidine hydrochloride-monohydrate, L-isoleucine, L-leucine, L-lysine hydrochloride, L-methionine, L-phenylalanine, L-proline, L-serine, L-threonine, L-tryptophan, L-tyrosine disodium dihydrate, L-valine, L-histidine, L-tyrosine disodium salt, and a mixture thereof.

In the present invention, an amino acid serves as a source of protein synthesis to be used for cell growth.

The amino acid may be comprised in an amount of from 0.111 to 0.161 wt % based on the total weight of the composition, for example, 1.110 to 1.606 g/L. By comprising an amino acid within the above range, the composition can aid the growth and maintenance of cells, and improve the stability of a formulation.

The vitamin may be a vitamin component used in a conventional animal cell culture medium, and may be selected from the group consisting of, for example, biotin, calcium D-pantothenate, folic acid, niacinamide, pyridoxine hydrochloride, riboflavin, thiamine hydrochloride, vitamin B12, choline chloride, i-inositol, ascorbic acid and a mixture thereof.

In the present invention, a vitamin plays a role in maintaining a cell activity.

The vitamin may be comprised in an amount of 0.0027 to 0.0060 wt % based on the total weight of the composition, for example 0.027 to 0.060 g/L. By comprising a vitamin within the above range, the composition can aid the maintenance of a cell activity.

The carbon source may be a carbon source component used in a conventional animal cell culture medium, and may be selected from the group consisting of, for example, D-glucose (dextrose), sodium pyruvate, hyphoxanthin Na, thymidine, linoleic acid, lipoic acid, adenosine, cytidine, guanosine, uridine, 2'-deoxyadenosine, 2'-deoxycytidine HCl, 2'-deoxyguanosine, and a mixture thereof.

In the present invention, the carbon source serves as an energy source, and in particular, in case of sodium bicarbonate, it may play a role in maintaining the pH of a medium.

The carbon source may be comprised in an amount of 0.120 to 0.463 wt % based on the total weight of the composition, for example, 1.201 to 4.625 g/L. By comprising the carbon source within the above range, the composition is not short of an energy source and thus can aid the growth of cells, and the formulation stability can be improved.

The inorganic salt may be an inorganic salt component used in a conventional animal cell culture medium, and may be selected from the group consisting of, for example, calcium chloride ($CaCl_2$) (anhydrous), copper sulfate pentahydrate ($CuSO_4\text{-}5H_2O$), ferric sulfate heptahydrate ($FeSO_4\text{-}7H_2O$), magnesium chloride (anhydrous), magnesium sulfate ($MgSO_4$) (anhydrous), potassium chloride (KCl), sodium chloride (NaCl), disodium hydrogen phosphate ($Na_2HPO_4$) anhydrous, sodium hydrogen phosphate monohydrate ($NaH_2PO_4\text{-}H_2O$), zinc sulfate heptahydrate ($ZnSO_4\text{-}7H_2O$), ferric nitrate nonahydrate ($Fe(NO_3)_3 \cdot 9H_2O$), sodium bicarbonate ($NaHCO_3$), and a mixture thereof.

In the present invention, an inorganic salt plays a role in regulating a cell function.

The inorganic salt may be comprised in an amount of 0.984 to 1.092 wt % based on the total weight of the composition, for example, 9.838 to 10.923 g/L. By comprising an inorganic salt within the above range, the composition can aid the regulation of a cell function and does not cause difficulty in formulating into a drug or cosmetics.

A cosmetic composition of the present invention may be directly applied to a skin for the purpose of improving a skin condition.

The cosmetic composition may be formulated into a cosmetic formulation conventionally prepared in the art. The cosmetic composition may be formulated, for example, into solution, suspension, emulsion, paste, gel, cream, lotion, powder, soap, surfactant-containing cleansing, oil, powder foundation, emulsion foundation, wax foundation, spray, and the like, but the present invention is not limited thereto. More specifically, the cosmetic composition can be formulated into soft lotion, nutritional lotion, nutritional cream, massage cream, essence, eye cream, cleansing cream, cleansing foam, cleansing water, pack, spray or powder.

When the formulation of a cosmetic composition of the present invention is a paste, a cream or a gel, it may comprise a carrier component selected from the group consisting of animal oil, vegetable oil, wax, paraffin, starch, tragacanth, cellulose derivatives, polyethylene glycol, silicone, bentonite, silica, talc, zinc oxide, and a mixture thereof.

When the formulation of a cosmetic composition of the present invention is a powder or a spray, it may contain a carrier component selected from the group consisting of lactose, talc, silica, aluminum hydroxide, calcium silicate, polyamide powder and a mixture thereof. In particular, when it is a spray, it may further contain chlorofluorohydrocarbons, propane/butane, dimethyl ether, and the like.

When the formulation of a cosmetic composition of the present invention is a solution or an emulsion, may comprise it may contain a carrier component selected from the group consisting of a solvent, a solvate, an emulsifier and a mixture thereof. Examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, sorbitan fatty acid ester, and a mixture thereof.

When the formulation of a cosmetic composition of the present invention is a suspension, it may comprise a carrier component selected from the group consisting of a liquid diluent (such as water, ethanol or propylene glycol), a suspension (such as ethoxylated isostearyl alcohol, polyoxyethylene sorbitol ester and polyoxyethylene sorbitan ester), microcrystalline cellulose, aluminum metahydroxide, bentonite, agar, tragacanth, and a mixture thereof.

When the formulation of a cosmetic composition of the present invention is a surfactant-containing cleansing, it may comprise a carrier component selected from the group consisting of aliphatic alcohol sulfate, aliphatic alcohol ether sulfate, sulfosuccinic acid monoester, isethionate, imidazolinium derivative, methyl taurate, sarcosinate, fatty acid amide ether sulfate, alkyl amidobetaine, aliphatic alcohol, fatty acid glyceride, fatty acid diethanolamide, vegetable oil, lanolin derivative, ethoxylated glycerol fatty acid ester, and a mixture thereof.

The term "carrier component" in a cosmetic composition of the present invention refers to a compound or composition already known which may be comprised in a cosmetic formulation and is not toxic, unstable or irritating beyond the level to which is the human body can adapt upon contact with skin.

A cosmetic composition of the present invention may further comprise, in addition to a carrier component, a supplementary agent selected from the group consisting of an antioxidant, a stabilizer, a solubilizer, a moisturizer, a pigment, a fragrance, a UV blocker, a colorant, a surfactant and a combination thereof. The supplementary agent is not limited as long as it is a supplementary agent conventionally used in preparing a cosmetic composition.

In addition, the present invention provides a pharmaceutical composition for preventing or treating a skin disorder comprising a) a cell culture medium; b) 0.4 to 0.8 ng/mL of epidermal growth factor (EGF); and c) 10 to 1,000 µg/mL of bovine serum albumin (BSA).

The effective component of the pharmaceutical composition of the present invention is the same as that of the cosmetic composition as described above.

The pharmaceutical composition of the present invention may prevent or treat inflammatory skin disorders selected from the group consisting of atopic dermatitis, allergy, skin eczema, acne, psoriasis, and a combination thereof.

Accordingly, the present invention provides a method for preventing or treating a skin disorder using the pharmaceutical composition.

In addition, the present invention provides a use of the pharmaceutical composition in preparing a drug for preventing or treating a skin disorder.

The method may comprise a step of applying the pharmaceutical composition of the present invention to the skin of a subject in need thereof. The subject may be a mammal, specifically a human.

A pharmaceutical composition of the present invention, in addition to an effective component, may further comprise a pharmaceutically acceptable carrier as needed.

The pharmaceutically acceptable carrier may be one conventionally used in preparing a drug, which may include lactose, dextrose, sucrose, sorbitol, mannitol, starch, rubber acacia, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil and the like, but is not limited thereto.

In addition, a pharmaceutical composition of the present invention may further comprise one or more pharmaceutically acceptable additives selected from the group consisting of lubricants, humectants, sweeteners, flavoring agents, emulsifying agents, suspending agents, preservatives, and a combination thereof.

The carrier may be comprised in an amount of about 1 wt % to about 99.99 wt %, preferably about 90 wt % to about 99.99 wt %, based on the total weight of the pharmaceutical composition of the present invention, and the pharmaceutically acceptable additive may be comprised in an amount of about 0.1 wt % to about 20 wt %.

A pharmaceutical composition of the present invention may be administered orally or parenterally, and preferably administered directly to the skin in a topical manner.

The dosage form of a pharmaceutical composition of the present invention may be in the form of an external preparation for skin such as transdermally-administered injection, ointment, solution, cream, spray, patch, and the like.

The appropriate dosage of a pharmaceutical composition of the present invention is determined considering various factors such as formulation method, administration method, age, body weight, sex, and pathological condition of a patient, food, administration time, administration route, excretion rate and responsiveness, and thus, the dosage should not be construed as limiting the scope of the invention in any aspect.

MODE FOR THE INVENTION

Hereinafter, the present invention will be described in more detail based on the following examples. The following examples are intended to illustrate the present invention, but the scope of the present invention is not limited thereto.

Example 1

A composition for improving a skin condition was prepared by adding 0.8 ng/mL of EGF and 100 μg/mL of BSA to FBS-free DMEM/F12 medium which has the composition shown in Table 1 below.

Example 2

A composition for improving skin condition was prepared by adding 0.4 ng/mL of EGF and 100 μg/mL of BSA to FBS-free DMEM/F12 medium which has the composition shown in Table 1 below.

Example 3

A composition for improving a skin condition was prepared by adding 0.6 ng/mL of EGF and 100 μg/mL of BSA to FBS-free DMEM/F12 medium which has the composition shown in Table 1 below.

Example 4

A composition for improving a skin condition was prepared by adding 0.8 ng/mL of EGF and 10 μg/mL of BSA to FBS-free DMEM/F12 medium which has the composition shown in Table 1 below.

Example 5

A composition for improving a skin condition was prepared by adding 0.8 ng/mL of EGF and 1,000 μg/mL of BSA to FBS-free DMEM/F12 medium which has the composition shown in Table 1 below.

TABLE 1

| Composition of FBS-free DMEM/F12 medium | |
|---|---|
| Composition | Concentration (g/L) |
| Glycine | 0.01875 |
| L-alanine | 0.00445 |
| L-arginine hydrochloride | 0.1475 |
| L-asparagine-monohydrate | 0.0075 |
| L-aspartic acid | 0.00665 |
| L-cysteine hydrochloride-monohydrate | 0.01756 |
| L-cysteine 2HCl | 0.03129 |
| L-glutamic acid | 0.00735 |
| L-glutamine | 0.365 |
| L-histidine hydrochloride-monohydrate | 0.03148 |
| L-isoleucine | 0.05447 |
| L-leucine | 0.05905 |
| L-lysine hydrochloride | 0.09125 |
| L-methionine | 0.01724 |
| L-phenylalanine | 0.03548 |
| L-proline | 0.01725 |
| L-serine | 0.02625 |
| L-threonine | 0.05345 |
| L-tryptophan | 0.00902 |
| L-tyrosine disodium dihydrate | 0.05579 |
| L-valine | 0.05285 |
| Biotin | 0.000003 |
| Calcium D-pantothenate | 0.00224 |
| Folic acid | 0.00265 |
| Niacinamide | 0.00202 |
| Pyridoxine hydrochloride | 0.00213 |
| Riboflavin | 0.00219 |
| Thiamine hydrochloride | 0.00217 |
| Vitamin B12 | 0.00068 |
| i-inositol | 0.0126 |
| Calcium chloride ($CaCl_2$) (anhydrous) | 0.1166 |
| Copper sulfate pentahydrate ($CuSO_4$—$5H_2O$) | 0.000001 |
| Ferric sulfate heptahydrate ($FeSO_4$—$7H_2O$) | 0.000417 |
| Magnesium chloride (anhydrous) | 0.02864 |
| Magnesium sulfate ($MgSO_4$) (anhydrous) | 0.04884 |
| Potassium chloride (KCl) | 0.3118 |
| Sodium bicarbonate ($NaHCO_3$) | 2.438 |
| Sodium chloride (NaCl) | 6.9955 |
| Disodium hydrogen phosphate ($Na_2HPO_4$) anhydrous | 0.07102 |
| Sodium hydrogen phosphate monohydrate ($NaH_2PO_4$—$H_2O$) | 0.0625 |
| Zinc sulfate heptahydrate ($ZnSO_4$—$7H_2O$) | 0.000432 |
| D-glucose (dextrose) | 3.151 |
| Hypoxanthin Na | 0.00239 |
| Linoleic acid | 0.000042 |
| Lipoic acid | 0.000105 |
| Sodium pyruvate | 0.055 |
| Thymidine | 0.000365 |

Example 6

A composition for improving a skin condition was prepared by adding 0.8 ng/mL of EGF and 100 μg/mL of BSA to a FBS-free DMEM medium which has the composition shown in Table 2 below.

TABLE 2

Composition of FBS-free DMEM medium

| Composition | Concentration (g/L) |
|---|---|
| Glycine | 0.03 |
| L-arginine hydrochloride | 0.084 |
| L-cysteine 2HCl | 0.063 |
| L-glutamine | 0.584 |
| L-histidine hydrochloride-monohydrate | 0.042 |
| L-isoleucine | 0.105 |
| L-leucine | 0.105 |
| L-lysine hydrochloride | 0.146 |
| L-methionine | 0.03 |
| L-phenylalanine | 0.066 |
| L-serine | 0.042 |
| L-threonine | 0.095 |
| L-tryptophan | 0.016 |
| L-tyrosine disodium salt dihydrate | 0.104 |
| L-valine | 0.094 |
| Choline chloride | 0.004 |
| Calcium D-pantothenate | 0.004 |
| Folic acid | 0.004 |
| Niacinamide | 0.004 |
| Pyridoxine hydrochloride | 0.004 |
| Riboflavin | 0.0004 |
| Thiamine hydrochloride | 0.004 |
| i-inositol | 0.0072 |
| Calcium chloride ($CaCl_2$) (anhydrous) | 0.2 |
| Ferric nitrate nonahydrate ($Fe(NO_3)_3 \cdot 9H_2O$) | 0.0001 |
| Magnesium sulfate ($MgSO_4$) (anhydrous) | 0.09767 |
| Potassium chloride (KCl) | 0.4 |
| Sodium bicarbonate ($NaHCO_3$) | 3.7 |
| Sodium chloride (NaCl) | 6.4 |
| Sodium hydrogen phosphate monohydrate ($NaH_2PO_4$—$H_2O$) | 0.125 |
| D-glucose (dextrose) | 4.5 |
| Sodium pyruvate | 0.11 |

Example 7

A composition for improving a skin condition was prepared by adding 0.8 ng/mL of EGF and 100 μg/mL of BSA to FBS-free MEM α medium which has the composition shown in Table 3 below.

TABLE 3

Composition of FBS-free MEM α medium

| Composition | Concentration (g/L) |
|---|---|
| Glycine | 0.05 |
| L-alanine | 0.025 |
| L-arginine hydrochloride | 0.105 |
| L-asparagine-monohydrate | 0.05 |
| L-aspartic acid | 0.03 |
| L-cysteine hydrochloride-monohydrate | 0.1 |
| L-cysteine 2HCl | 0.031 |
| L-glutamic acid | 0.075 |
| L-glutamine | 0.292 |
| L-histidine | 0.031 |
| L-isoleucine | 0.0524 |
| L-leucine | 0.052 |
| L-lysine | 0.073 |
| L-methionine | 0.015 |
| L-phenylalanine | 0.032 |
| L-proline | 0.04 |
| L-serine | 0.025 |
| L-threonine | 0.048 |
| L-tryptophan | 0.01 |
| L-tyrosine disodium salt | 0.052 |
| L-valine | 0.046 |
| Ascorbic acid | 0.05 |
| Biotin | 0.0001 |
| Choline chloride | 0.001 |
| Calcium D-pantothenate | 0.001 |
| Folic acid | 0.001 |
| Niacinamide | 0.001 |
| Pyridoxal hydrochloride | 0.001 |
| Riboflavin | 0.0001 |
| Thiamine hydrochloride | 0.001 |
| Vitamin B12 | 0.00136 |
| i-inositol | 0.002 |
| Calcium chloride ($CaCl_2$) (anhydrous) | 0.2 |
| Magnesium sulfate ($MgSO_4$) (anhydrous) | 0.09767 |
| Potassium chloride (KCl) | 0.4 |
| Sodium bicarbonate ($NaHCO_3$) | 2.2 |
| Sodium chloride (NaCl) | 6.8 |
| Sodium hydrogen phosphate monohydrate ($NaH_2PO_4$—$H_2O$) | 0.14 |
| Adenosine | 0.01 |
| Cytidine | 0.01 |
| Guanosine | 0.01 |
| Uridine | 0.01 |
| 2'-deoxyadenosine | 0.01 |
| 2'-deoxycytidine HCl | 0.011 |
| 2'-deoxyguanosine | 0.01 |
| Thymidine | 0.01 |
| D-glucose (dextrose) | 1 |
| Lipoic acid | 0.0002 |
| Sodium pyruvate | 0.11 |

Comparative Examples 1 and 2

Compositions were prepared by adding 1 ng/mL or 20 ng/mL of EGF only to FBS-free DMEM/F12 medium which has the composition shown in Table 1, respectively.

Comparative Examples 3 and 4

Compositions were prepared by adding 1 ng/mL or 20 ng/mL of EGF only to a FBS-free DMEM medium which has the composition shown in Table 2, respectively.

Comparative Examples 5 and 6

Compositions were prepared by adding 1 ng/mL or 20 ng/mL of EGF only to FBS-free MEM α medium which has the composition shown in Table 3, respectively.

The compositions according to the above Examples and Comparative Examples are summarized in Table 4 below.

TABLE 4

| | Examples | | | | | | | Comparative Examples | | | | | |
|---|---|---|---|---|---|---|---|---|---|---|---|---|---|
| | 1 | 2 | 3 | 4 | 5 | 6 | 7 | 1 | 2 | 3 | 4 | 5 | 6 |
| Medium (FBS-free) | DMEM/F12 | | | | | DMEM | MEM α | DMEM/F12 | | DMEM | | MEM α | |
| EGF (ng/mL) | 0.8 | 0.4 | 0.6 | 0.8 | 0.8 | 0.8 | 0.8 | 1 | 20 | 1 | 20 | 1 | 20 |
| BSA (µg/mL) | 100 | 100 | 100 | 10 | 1000 | 100 | 100 | — | — | — | — | — | — |

Experimental Example 1: Comparison of Cell Proliferation Rates

Human dermal fibroblast cells (Korean Cell Line Bank) under culture in a culture dish were treated with trypsin 0.05% (w/v) and separated from the culture dish. $3 \times 10^3$ of the separated human dermal fibroblast cells were mixed with 100 µl of FBS-free DMEM/F12 medium which has the composition shown in Table 1, and then put into each well of a 96-well plate. After culturing in an incubator in a condition of 37° C. and 5% $CO_2$ for one day, the existing culture medium was removed when the cells were completely attached to the bottom of the 96-well plate. And then, the wells were treated with the compositions of Example 1, Comparative Example 1 or Comparative Example 2, respectively. As a negative control, FBS-free DMEM/F12 medium containing no EGF and BSA was used.

The mixtures were incubated for 24 hours, 48 hours, and 72 hours in an incubator in a condition of 37° C. and 5% $CO_2$, and then, additives were removed using a suction machine, and the remaining culture solution was completely removed from the 96-well plate with sterilized phosphate buffered saline (PBS).

To verify the cell proliferation, 10 µL of CCK-8 reaction solution (Dojindo) was added to each well and reacted at 37° C. for 2 hours. Thereafter, the absorbance was measured at 450 nm using a Model 680 microplate reader (Bio-rad, CA, USA).

The comparative results of absorbance values of each well based on the absorbance values of the cells grown in the culture medium not containing cytokine, i.e., the negative control, were shown in FIG. 1.

As shown in FIG. 1, the group treated with the composition of Example 1 did not show cytotoxicity, indicating that the cell proliferation rate was excellent. In particular, it was verified that the cell proliferation rate was improved more than the group treated with the composition of Comparative Example 2 to which EGF was added at a high concentration of 20 ng/mL after 72 hours of culturing.

Experimental Example 2: Evaluation of Collagen Synthesis Effect

Human dermal fibroblast cells (Korean Cell Line Bank) isolated from human skin tissue were cultured in DMEM/F12 medium (Gibco) containing 10% FBS and 1% penicillin-streptomycin in 5% $CO_2$ condition, and then, $3 \times 10^5$ cells of the cultured cells were seeded on a 6-well plate. On the next day, the cultured cells were washed once using PBS, and then the medium was replaced with FBS-free DMEM/F12 medium. The cells were treated with the compositions of Example 1, Comparative Example 1 or Comparative Example 2 and cultured for 24 hours.

After completion of the reactions, the cell culture solutions were collected and subjected to ELISA analysis for type III collagen (CUSABIO Biotech Co., Wuhan, China) to determine each collagen synthesis concentration. ELISA analysis was performed according to the guideline provided by the company included in the kit. The results are shown in FIG. 2.

As shown in FIG. 2, the group treated with the composition of Example 1 showed the best collagen synthesis capcapability, which was similar to the group treated with the composition of Comparative Example 2 in which EGF was added at a high concentration of 20 ng/mL.

Experimental Example 3: Verification of Migration of Human Dermal Fibroblast Cells In order to investigate the wound healing capability of a composition of the present invention, the migration capability of human dermal fibroblast cells was verified.

First, $6 \times 10^4$ cells/mL of human dermal fibroblast cells (Korean Cell Line Bank) were seeded into IBIDI Culture insert (Ibidi GmbH, M, Germany) chamber consisting of two reservoirs separated by 70 µm septum. Then the cells in the chamber were cultured for 12 hours in the condition of 5% $CO_2$ and 37° C.

The cultured cells were treated with the compositions of Example 1, Comparative Example 1 and Comparative Example 2, respectively. FIG. 3 provides photographic images obtained by an inverted microscope (Olympus) which shows the degrees of cell migrations before and 9 hours after the composition treatments.

Using T-Scratch software (Computational Science & Engineering Laboratory, ETH Zurich, Switzerland), the images were analyzed to calculate the cell migration rate of each treatment group as the ratio (%) of cell-covered area based on the result of the negative control set at 100%. The results are shown in FIG. 4.

As shown in FIGS. 3 and 4, the group treated with the composition of Example 1 showed the best wound healing capability, which was similar to the group treated with the composition of Comparative Example 2 in which EGF was added at a high concentration of 20 ng/mL.

Also, the verification results of the wound healing capability using the compositions of Example 6, and Comparative Examples 3 and 4 in the same manner as described above were shown in FIGS. 5 and 6. Also, the verification results of the wound healing capability using the compositions of Example 7, and Comparative Examples 5 and 6 in the same manner as described above were shown in FIGS. 7 and 8.

As shown in FIGS. 5 and 6, and FIGS. 7 and 8, the groups respectively treated with the compositions of Examples 6 and 7 prepared by simultaneously adding EGF and BSA to FBS-free DMEM medium or FBS-free MEM α medium showed the best wound healing capabilities, which were similar to the groups treated with the compositions of Comparative Examples 4 and 6 in where 20 ng/mL EGF was added alone.

Meanwhile, experiments were conducted in the same manner as described above using the compositions of Examples 1 to 3 and Comparative Examples 1 and 2 in order to verify the wound healing capability depending on the amount of EGF in a composition of the present invention. The results were shown in FIGS. 9 and 10. As shown in FIGS. 9 and 10, all of the groups respectively treated with the compositions of Examples 1 to 3 containing 0.4 to 0.8 ng/mL of EGF showed up to 50% improved effect as compared to the negative control group, which was similar to the group treated with the composition of Comparative Example 2 where 20 ng/mL EGF alone was added.

Also, experiments were conducted in the same manner as described above using the compositions of Examples 1, 4 and 5, and Comparative Examples 1 and 2 in order to verify the wound healing capability depending on the amount of BSA in a composition of the present invention. The results were shown in FIGS. 11 and 12.

As shown in FIGS. 11 and 12, all of the groups respectively treated with the compositions of Examples 1, 4 and 5 containing 10 to 1,000 µg/mL of BSA showed up to 40% improved effect as compared to the negative control group, which was similar to the group treated with the composition of Comparative Example 2 where an excessive amount of 20 ng/mL EGF alone was added.

These results demonstrate that a composition of the present invention containing a combination of EGF and BSA exhibits superior collagen synthesis and cell regeneration effect compared to the composition containing excessive EGF alone.

Therefore, a composition of the present invention does not show cytotoxicity and increases collagen synthesis even when a small amount of EGF is contained. Such composition exhibits excellent skin regeneration effect by improved wound healing capability as well as wrinkle-improving effect. In addition, such composition not only is superior in price competitiveness by decreasing the production cost to about 1/20, but also significantly reduces cancer incidence arising from the excessive use of EGF, and thus it can be safely applied to a living body.

The invention claimed is:

1. A method for improving a skin condition of a subject in need thereof, comprising applying to skin of the subject a composition comprising:
   a) a cell culture medium;
   b) 0.4 to 0.8 ng/mL of epidermal growth factor (EGF); and
   c) 10 to 100 µg/mL of bovine serum albumin (BSA),
   wherein the a) cell culture medium is a fetal bovine serum-free medium,
   wherein the improvement of a skin condition is selected from the group consisting of inhibition of wrinkle occurrence, inhibition of skin aging, improvement of skin elasticity, skin regeneration, injury or wound healing, and a combination thereof; and
   wherein the subject in need thereof is a mammal.

2. The method of claim 1, wherein the cell culture medium is a mammalian cell culture medium.

3. The method of claim 2, wherein the mammalian cell culture medium is selected from the group consisting of DMEM/F-12 (Dulbecco's Modified Eagle's Medium/Nutrient Mixture F-12), DMEM, and MEM α (Minimum Essential Medium α).

4. The method of claim 1, wherein the composition further comprises a component selected from the group consisting of an amino acid, a vitamin, a carbon source, an inorganic salt, and a combination thereof.

5. The method of claim 4, wherein the amino acid is selected from the group consisting of glycine, L-alanine, L-arginine hydrochloride, L-asparagine-monohydrate, L-aspartic acid, L-cysteine hydrochloride-monohydrate, L-cysteine 2HCl, L-glutamic acid, L-glutamine, L-histidine hydrochloride-monohydrate, L-isoleucine, L-leucine, L-lysine hydrochloride, L-methionine, L-phenylalanine, L-proline, L-serine, L-threonine, L-tryptophan, L-tyrosine disodium dihydrate, L-valine, L-histidine, L-tyrosine disodium salt, and a mixture thereof.

6. The method of claim 4, wherein the vitamin is selected from the group consisting of biotin, calcium D-pantothenate, folic acid, niacinamide, pyridoxine hydrochloride, riboflavin, thiamine hydrochloride, vitamin B12, choline chloride, i-inositol, ascorbic acid and a mixture thereof.

7. The method of claim 4, wherein the carbon source is selected from the group consisting of D-glucose (dextrose), sodium pyruvate, hyphoxanthin Na, thymidine, linoleic acid, lipoic acid, adenosine, cytidine, guanosine, uridine, 2'-deoxyadenosine, 2'-deoxycytidine HCl, 2'-deoxyguanosine, and a mixture thereof.

8. The method of claim 4, wherein the inorganic salt is selected from the group consisting of anhydrous calcium chloride ($CaCl_2$), copper sulfate pentahydrate ($CuSO_4$-$5H_2O$), ferric sulfate heptahydrate ($FeSO_4$-$7H_2O$), anhydrous magnesium chloride, anhydrous magnesium sulfate ($MgSO_4$), potassium chloride (KCl), sodium chloride (NaCl), anhydrous disodium hydrogen phosphate ($Na_2HPO_4$), sodium hydrogen phosphate monohydrate ($NaH_2PO_4$-$H_2O$), zinc sulfate heptahydrate ($ZnSO_4$-$7H_2O$), ferric nitrate nonahydrate ($Fe(NO_3)_3$·$9H_2O$), sodium bicarbonate ($NaHCO_3$), and a mixture thereof.

9. The method of claim 4, wherein the composition comprises 1.110 to 1.606 g/L of an amino acid, 0.027 to 0.060 g/L of a vitamin, 1.201 to 4.625 g/L of a carbon source and 9.838 to 10.923 g/L of an inorganic salt.

10. The method of claim 1, wherein the mammal is human.

* * * * *